United States Patent
Goulait et al.

[19]

[11] Patent Number: 5,487,809
[45] Date of Patent: Jan. 30, 1996

[54] METHOD FOR MANUFACTURING TAPE TAB STOCK THAT MAY BE USED TO PRODUCE TAPE TAB FASTENERS FOR DISPOSABLE ABSORBENT ARTICLES

[75] Inventors: David J. K. Goulait; David W. Cabell, both of Cincinnati, Ohio

[73] Assignee: The Procter & Gamble Company, Cincinnati, Ohio

[21] Appl. No.: 263,115

[22] Filed: Jun. 21, 1994

[51] Int. Cl.⁶ .............................. B32B 31/18; B32B 31/08
[52] U.S. Cl. ............................ 156/259; 156/66; 156/216; 156/226; 156/264; 156/269; 156/270; 156/271; 604/389; 604/390
[58] Field of Search .................................. 604/389, 390; 156/66, 259, 271, 216, 226, 264, 269

[56] References Cited

U.S. PATENT DOCUMENTS

| | | | |
|---|---|---|---|
| 3,862,634 | 1/1975 | Small | 128/284 |
| 3,893,460 | 7/1975 | Karami . | |
| 3,897,293 | 7/1975 | Babcock . | |
| 4,144,887 | 3/1979 | Milnamow . | |
| 4,491,493 | 1/1985 | Eaton . | |
| 4,531,992 | 7/1985 | Eaton . | |
| 4,576,600 | 3/1986 | Joa | 604/390 |
| 5,004,630 | 4/1991 | Polski . | |
| 5,021,111 | 1/1991 | Swenson | 156/264 |
| 5,106,384 | 4/1992 | Polski . | |
| 5,264,264 | 11/1993 | Shibata et al. . | |
| 5,288,546 | 2/1994 | Roessler et al. . | |
| 5,322,607 | 7/1994 | Nakamura et al. . | |
| 5,342,685 | 8/1994 | Gobran | 428/355 |
| 5,399,177 | 3/1995 | Blaney et al. | 604/389 |
| 5,399,219 | 3/1995 | Roessler et al. | 156/259 |

FOREIGN PATENT DOCUMENTS

| | | |
|---|---|---|
| 4-226183 | 8/1992 | Japan . |
| 93/22996 | 11/1993 | WIPO . |

*Primary Examiner*—David A. Simmons
*Assistant Examiner*—M. Curtis Mayes
*Attorney, Agent, or Firm*—David M. Weirich; Steven W. Miller; E. Kelly Linman

[57] ABSTRACT

A method for manufacturing tape tab stock that may be used to produce tape tabs for use with disposable absorbent articles, as well as a method for manufacturing tape tab stock that can be produced on-line and concurrently with the disposable absorbent article to which the tape tabs are joined. The first step in the process is to provide a backing substrate upon which the adhesives of the tape tab can be applied. Once the backing is provided, a pressure sensitive adhesive is applied to regions of one side of the backing substrate. The backing substrate is then slit in a direction parallel to the machine direction and the release surface of a release substrate is placed in contact with the pressure sensitive adhesive, forming a laminate comprising the backing substrate and the release substrate. The release substrate preferably covers the entire surface of the backing substrate upon which pressure sensitive adhesive has been applied. The surface of the laminate, including the surface of the release substrate that is not in contact with the pressure sensitive adhesive, and any of the backing substrate not covered by the release substrate is then coated with a second adhesive for joining the tape tabs to the absorbent article. After the second adhesive is applied to the surface of the laminate, the laminate is slit in a direction parallel to the machine direction and either rewound for shipping or storage, or fed to a taper unit that is integrated into the absorbent article manufacturing line. The taper unit cuts individual tape tabs and applies them to the absorbent article chassis.

15 Claims, 4 Drawing Sheets

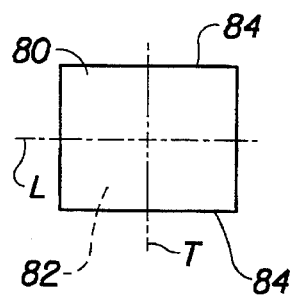
Fig. 3a
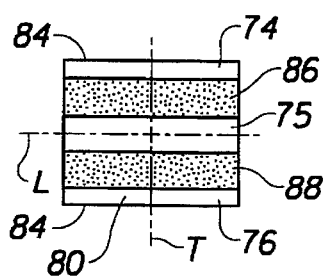
Fig. 3b
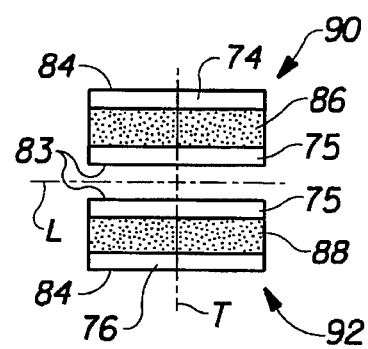
Fig. 3c
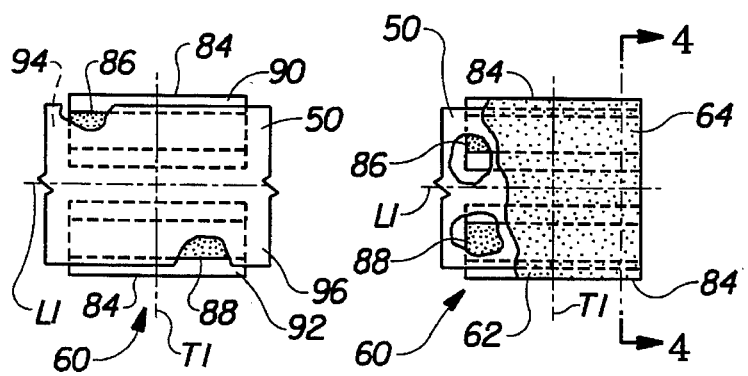
Fig. 3d
Fig. 3e
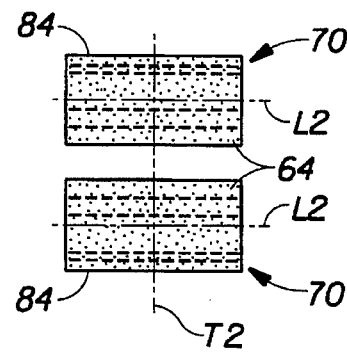
Fig. 3f

METHOD FOR MANUFACTURING TAPE TAB STOCK THAT MAY BE USED TO PRODUCE TAPE TAB FASTENERS FOR DISPOSABLE ABSORBENT ARTICLES

FIELD OF THE INVENTION

The present invention relates to a method for manufacturing tape tab stock that may be used to produce tape tabs for use with disposable absorbent articles comprising tape tab closure members, and a method for manufacturing tape tab stock that can be produced on-line and concurrently with the disposable absorbent articles to which the tape tabs are to be joined.

BACKGROUND OF THE INVENTION

Disposable absorbent articles, such as diapers, training pants, incontinence garments, feminine hygiene garments and the like have become very popular in the market place today. Typically, adhesive tape tabs fasteners are used to secure the absorbent articles about the waist of the wearer. Such fasteners are generally manufactured separately from the absorbent articles to which they are attached. For example, it is common for the manufacture of tape tabs to take place in different facilities than the manufacture of the absorbent article chassis, and at a different time. Generally, tape tabs are manufactured by applying a release agent to a backing and winding the backing onto a roll. The roll of backing material treated with a release agent is then unwound and coated with pressure-sensitive adhesive, forming a tape stock. The tape stock is then rewound onto rolls for shipping. Finally, at the place of manufacture of the absorbent article, the tape stock is unwound, cut to size, and joined to the chassis of an absorbent article.

An overriding consideration in the construction of a disposable absorbent article is the cost of manufacturing the absorbent article. The present invention provides a reduced cost method for the manufacture of tape tabs for use with disposable absorbent articles. If desired, the tape tabs can be manufactured concurrently with the chassis of the absorbent articles and in the same location, thus eliminating the need to rewind the tape stock or prepare it for shipping. This also eliminates the need to coat the non-adhesive surface of the tape stock with a release agent, simplifying the process of manufacturing the tape tabs and reducing the overall cost of manufacturing the disposable absorbent articles.

It is an object of the present invention to provide a low cost method for manufacturing tape tab stock that may be used to produce tape tabs for use with disposable absorbent articles.

It is a further object of the present invention to provide a method for the on-line manufacture of tape tabs to be used with disposable absorbent articles.

These and other objectives of the present invention will be more readily apparent when considered in reference to the following description and when taken in conjunction with the accompanying drawings.

SUMMARY OF THE INVENTION

The present invention provides a method for the manufacture of tape tab stock that may be used to produce tape tabs for use with disposable absorbent articles, as well as a method for the on-line manufacture of tape tabs that may be manufactured concurrently with the chassis of the absorbent article to which the tape tabs will be attached. The first step is to provide a backing substrate upon which the adhesives of the tape tab can be applied. Once the backing is provided, a pressure-sensitive adhesive is applied to regions of one side of the backing substrate. (The pressure-sensitive adhesive preferably functions as the adhesive used to fasten an element of the absorbent article, such as a front waist region, to another element of the absorbent article, such as a rear waist region.) The backing substrate is then slit in a direction parallel to the machine direction and the release surface of a release substrate is placed in contact with the pressure-sensitive adhesive, forming a laminate comprising the backing substrate and the release substrate. The release substrate preferably covers the entire surface of the backing substrate upon which pressure-sensitive adhesive has been applied. However, in a preferred embodiment, at least a portion of the backing substrate extends outwardly in a direction parallel to the cross machine direction beyond the longitudinal edges of the release substrate. The surface of the laminate, including the surface of the release substrate that is not in contact with the pressure-sensitive adhesive, and any of the backing substrate not covered by the release substrate is then coated with a construction adhesive. (The construction adhesive is used to join the tape tabs to the absorbent article.) After the construction adhesive is applied to the surface of the laminate, the laminate is slit in a direction parallel to the machine direction and either rewound for shipping or storage, or fed to a taper unit that is integrated into the absorbent article manufacturing line. The taper unit cuts individual tape tabs and applies them to the absorbent article chassis.

The present invention provides a low cost method for manufacturing tape tab stock that may be used to produce tape tabs for use with absorbent articles. The method of the present invention eliminates the need to apply a release agent to the surface of the backing substrate to which no adhesive is applied. Further, the method of the present invention can be performed concurrently with the manufacture of the absorbent article to which the tape tabs are to be attached, thus, eliminating the need to rewind the tape stock. Therefore, a simplified and more economical process is provided for manufacturing tape tabs for use with disposable absorbent articles.

An alternative embodiment of the present invention provides a method for the manufacture of a one-piece tape tab. As above, a backing substrate is provided and a pressure-sensitive adhesive is applied to one surface of the backing substrate. The backing substrate is then slit in a direction parallel to the machine direction. However, rather than utilizing a separate release substrate to form a release surface for the pressure-sensitive adhesive of the tape tabs, the backing substrate comprises an integral release surface to which the pressure-sensitive adhesive of the tape tab may be releasably fastened.

BRIEF DESCRIPTION OF THE DRAWINGS

While the specification concludes with claims particularly pointing out and distinctly claiming the subject matter which is regarded as the present invention, it is believed that the invention will be better understood from the following description which is taken in conjunction with the accompanying drawings, in which:

FIGS. 3a–3f represent a plan view of the process for on-line manufacturing tape tabs for use with absorbent articles, showing the flow of the process in the machine direction.

DETAILED DESCRIPTION OF THE INVENTION

The method of the present invention is particularly suitable for manufacturing tape tabs for use with disposable absorbent articles. As used herein, the term "absorbent article" refers to devices which absorb and contain body exudates, and more specifically, refers to devices which are placed against the skin of a wearer to absorb and contain the various exudates discharged from the body. The term "disposable" is used herein to describe absorbent articles which are not intended to be laundered or otherwise restored or reused as an absorbent article after a single use (i.e. they are intended to be discarded, and preferably, recycled, composted or otherwise disposed of in an environmentally compatible manner). A "unitary" absorbent article refers to an absorbent article which is formed from separate parts united together to form a coordinated entity so that they do not require separate manipulative parts like a separate holder and liner. A preferred embodiment of a unitary absorbent article comprising tape tabs manufactured by the method of the present invention is the disposable absorbent article shown in FIG. 1. As used herein, the term "diaper" refers to an absorbent article generally worn by infants and incontinent persons that is generally worn about the lower torso of the wearer. It should be understood, however, that the present invention is also applicable to other absorbent articles such as incontinence briefs, diaper holders, feminine hygiene garments, training pants, and the like.

Figure 1:
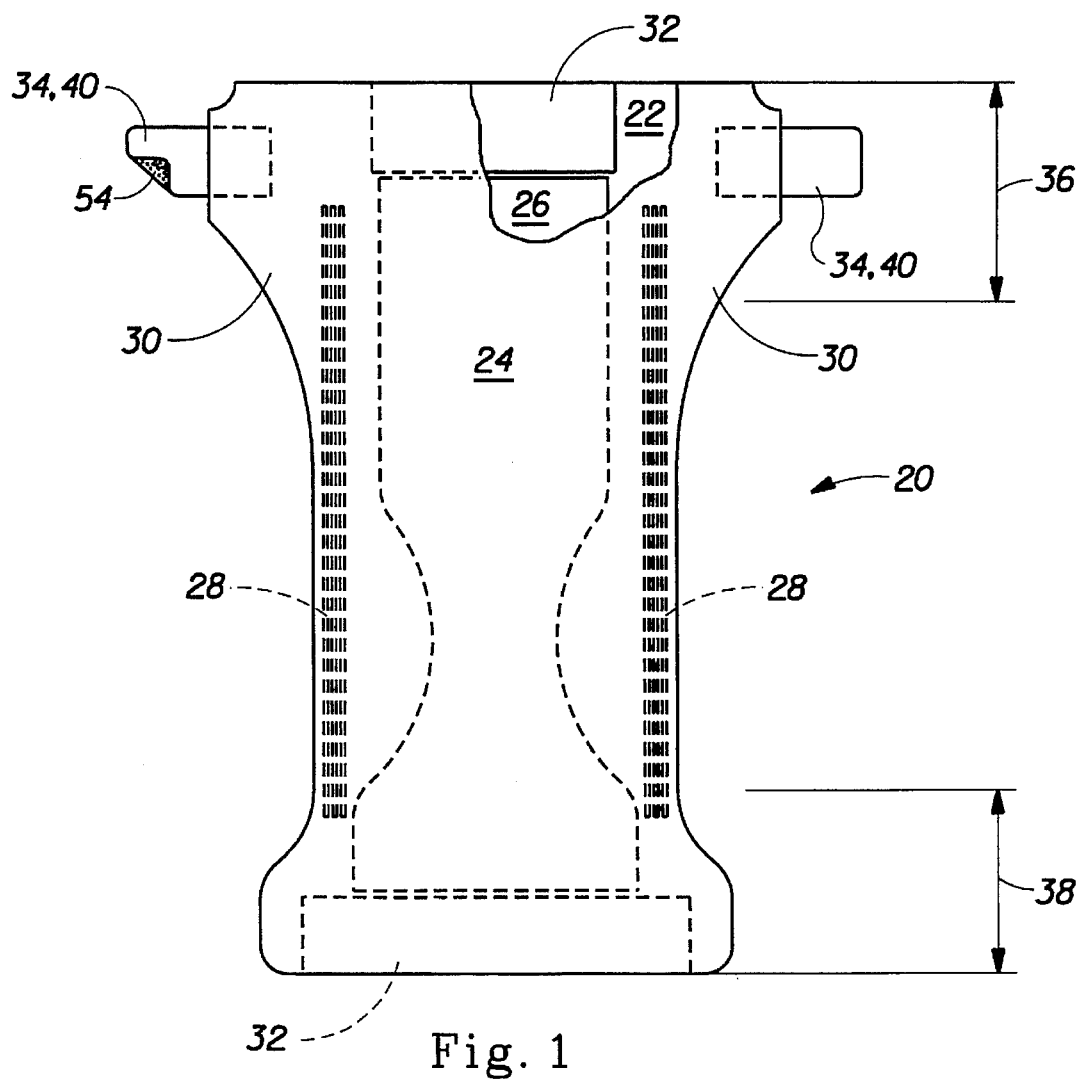
FIG. 1 is a plan view of an absorbent article comprising a tape tab manufactured by on-line process.

With reference to FIG. 1, an absorbent article, such as diaper 20, generally comprises a liquid permeable topsheet 22, a liquid impermeable backsheet 24, and an absorbent core 26 sandwiched between the topsheet 22 and the backsheet 24. The diaper 20 preferably further comprises a front waist region 36, a rear waist region 38, elasticized leg cuffs 28, ear flaps 30, an elastic waist feature 32 and a fastening system 34 comprising at least one tape tab 40. An example of a preferred absorbent article to which the tape tabs of the present invention may be joined is more fully and completely described in U.S. Pat. No. 5,151,092 entitled "Absorbent Article With Dynamic Elastic Waist Feature Having A Predisposed Resilient Flexural Hinge", issued to Buell et al. on Sep. 29, 1992 which is hereby incorporated by reference herein.

Overall method of on-line manufacture of tape tabs

The tape tabs 40 of the present invention are made by first providing a backing substrate upon which the adhesives of the tape tab 40 can be applied. A pressure-sensitive adhesive is applied to regions of one side of the backing substrate. (As described above, the pressure-sensitive adhesive preferably functions as the adhesive used to fasten an element of the absorbent article, such as the front waist region 36, to another element of the absorbent article, such as the rear waist region 38.) The backing substrate is then preferably slit in a direction parallel to the machine direction and a release substrate is placed in contact with the pressure-sensitive adhesive, forming a laminate comprising the backing substrate, the pressure-sensitive adhesive and the release substrate. The surface of the laminate, including the surface of the release substrate, as well as any portion of the backing substrate not covered by the release substrate is then coated with a construction adhesive for joining the tape tabs to the absorbent article. After the construction adhesive is applied to the surface of the laminate, the laminate is preferably slit in a direction parallel to the machine direction and fed to a taper unit that is integrated into the absorbent article manufacturing line. The taper unit cuts individual tape tabs 40 from the laminate and joins the tape tabs 40 to the chassis of the absorbent articles. This process is illustrated in FIGS. 2 and 3.

Figure 2:
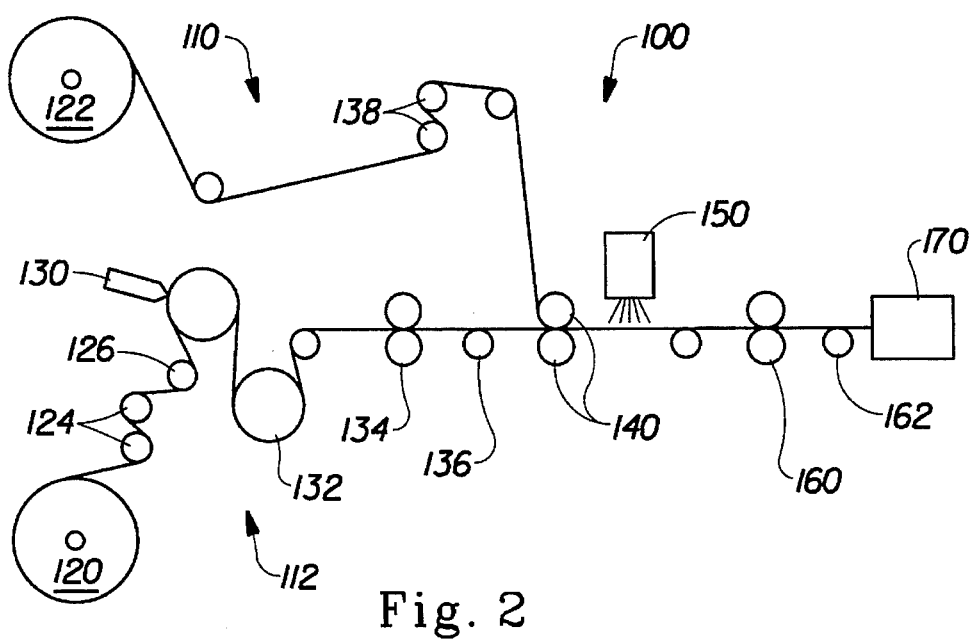
FIG. 2 is a representative side view of the process for on-line manufacturing tape tabs for use with absorbent articles.
Figure 4:
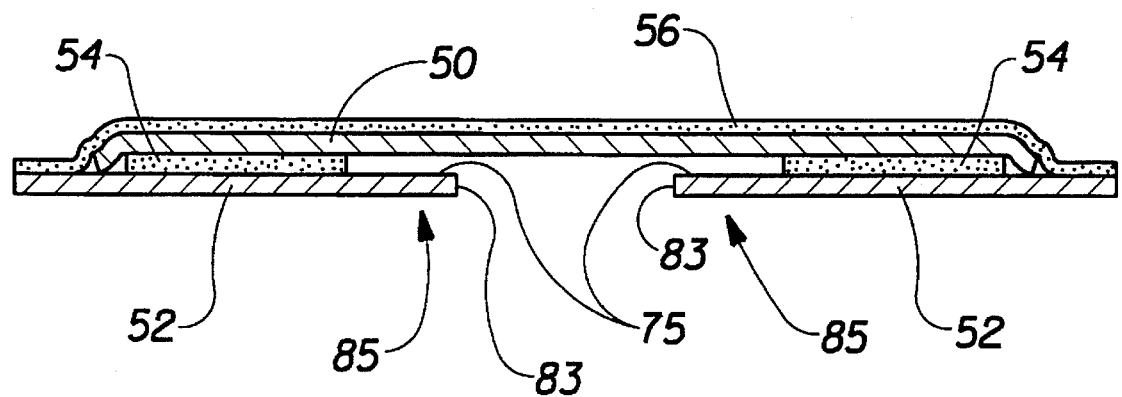
FIG. 4 is a cross-sectional view of the laminate shown in FIG. 3e.

The tape tabs 40 of the present invention may be produced on the apparatus 100, as shown in FIG. 2. The apparatus 100 comprises two separate process modules, process module 110 for providing a release substrate 50; and process module 112 for providing a backing substrate (or "backing") 52, applying a pressure-sensitive adhesive 54 to the backing 52 and slitting the backing 52 prior to contacting the release substrate 50 to the pressure-sensitive adhesive 54 disposed on the backing 52. In a preferred embodiment, the apparatus 100 is integrated into a disposable absorbent article manufacturing line such that the tape tabs 40 of the present invention are manufactured "on-line". (As used herein, the term "integrated" means interconnected process modules that operate concurrently to produce finished products from source materials. The term "on-line" is used to refer to the process of manufacturing the tape tabs 40 of the present invention on an apparatus that is integrated with the manufacturing line that produces the disposable absorbent articles to which the tape tabs will be joined.)

The backing substrate

Examining process module 112 in greater detail, a backing substrate 52 is provided and taken from the unwind roll 120. The backing substrate 52 may comprise any material to which a pressure-sensitive adhesive and a permanent adhesive, such as a hot melt adhesive, may be applied. Some nonlimiting examples of suitable backing substrates include films, laminates, woven and nonwoven webs, foams, and the like. In a preferred embodiment, the backing substrate 52 comprises a cellulose, polyolefin or polyester film ranging in thickness from about 2.5 mils to about 5.0 mils in thickness, more preferably about 4 mils in thickness. A polyolefin film that has been found to be particularly suitable for the backing substrate is the polypropylene film manufactured by the Exxon Chemical Company of Lake Zurich, Ill., under the trade name EX-377. A cellulose film that has been found to be suitable is manufactured by the Kimberly-Clark Corporation of Dallas Texas under the trade name C-49490.

As shown in FIG. 2, the backing substrate 52 is taken from the unwind roll 120 and passes through the S-wrap tensioning rolls 124 to provide proper tensioning and to prevent puckering or bunching of the backing 52. If necessary, a tracking system (not shown) as is commonly utilized and known in the art, may be employed in the process module 112 to optimally track and adjust the backing substrate 52 into the S-wrap tensioning rolls 124. A tracking system manufactured by the Fife Corporation of Oklahoma City, Okla., and sold as Model Op6 LRA may be suitable.

Guide roll 126 guides the backing 52 into position adjacent the adhesive slot coater 130 for application of the pressure-sensitive adhesive 54. The adhesive slot coater 130 may be any adhesive slot coater as is known in the art. Similarly, the pressure-sensitive adhesive 54 may be any pressure-sensitive adhesive as is known in the art, including, but not limited to the pressure-sensitive adhesives HL-1414 and HL-1350 manufactured by the H. B. Fuller Company of St. Paul Minn.; and H-2153 manufactured by the Findley Adhesive Corporation of Wauwatosa, Wis. The adhesive slot coater 130 preferably applies the pressure-sensitive adhesive 54 to the backing 52 in a heated, liquid state. After the pressure-sensitive adhesive 54 is applied, the backing 52 is preferably directed to a chill roll 132 such that the pressure-sensitive adhesive 54 is cooled and permitted to solidify on the surface of the backing 52.

Once the pressure-sensitive adhesive 54 has been applied, and preferably cooled, the backing 52 is preferably directed to a shear slitting apparatus 134 that slits the backing 52 in a direction parallel to the machine direction. (It should be noted, however, in less preferred embodiments, the backing 52 is not slit and separated. In such embodiments, a single piece of tape tab stock 70 results rather than the multiple segments as described more fully below with regard to the preferred embodiments.) The backing 52 is then separated laterally at the slit. (As used herein, the term "laterally" is defined as the direction perpendicular to the machine direction, or parallel to the cross machine direction.) The backing 52 may be separated by any means as are known in the art, including but not limited to any web spreader 136 as is known in the art.

The release substrate

The backing 52 comprising the pressure-sensitive adhesive 54 is directed to a nip between the combining rolls 140 where the surface of the backing 52 comprising the pressure-sensitive adhesive 54 is placed in contact with the release surface of a release substrate 50. The release substrate 50 generally comprises a base material and a release agent disposed on at least one surface of the base material. However, release substrates are available wherein the base material itself acts as a release agent, and thus, no other release agent is needed. The release agent may be applied to the base material "on-line", or premanufactured as shown in FIG. 2. The base material of the release substrate 50 may be any material as is known in the art, including, but not limited to films, laminates, woven and nonwoven webs, foams, and the like. Examples of suitable base materials for the release substrates of the present invention comprise cellulose materials or polypropylene films, ranging in thickness from 1.0 to 5.0 mils. One preferred base material for the release substrate 50 is the polypropylene film EX-399 manufactured by the Exxon Chemical Company of Lake Zurich, Ill. Another preferred base material for the release substrate 50 is the cellulose film 1224212 manufactured by the Rhinelander Paper Company of Rhinelander, Wis. The release agent may be any release agent as is known in the art that will act as a release agent for the particular pressure-sensitive adhesive 54 utilized. An example of a suitable release agent that works well with many different base materials and pressure-sensitive adhesives is silicone. The Goldschmidt Company of Essen, West Germany manufactures silicone formulas that can be used as release agents under the trade names RC711 or RC726. (In preferred embodiments, the release agent comprises a mixture of the RC711 and RC726 silicone formulas.)

As shown in FIG. 2, the release substrate 50 is taken from the unwind roll 122 and passes through the S-wrap tensioning rolls 138 to provide proper tensioning and to prevent puckering or bunching of the release substrate 50. If necessary, a tracking system (not shown) as is commonly utilized and known in the art, may be employed in the process module 110 to optimally track and adjust the release substrate 50 into the S-wrap tensioning rolls. As with the process module 112, a tracking system manufactured by the Fife Corporation of Oklahoma City, Okla., and sold as Model Op6 LRA may be suitable to ensure proper tracking of the release substrate 50 in the process module 110.

Joining the backing substrate with the release substrate

The surface of the backing substrate 52 comprising the pressure-sensitive adhesive 54 is contacted with the surface of the release substrate 50 comprising the release agent as the substrates pass through the nip between the combining rolls 140. The backing substrate 52 and the release substrate 50 become releasably joined together, forming a laminate 60. The laminate 60 is directed to pass adjacent an adhesive spray nozzle 150 where a construction adhesive 56 is applied to the surface of the laminate 60, forming a tape tab stock 70. The spray nozzle 150 may be any adhesive spray nozzle known in the art, including, but not limited to a J & M meltblown nozzle available from J & M Laboratories, Inc. of Dawsonville, Ga. or a Nordson spiral nozzle available from the Nordson Corporation of Norcross, Ga. Likewise, the construction adhesive 56 may be any adhesive known in the art, however, the construction adhesive 56 is preferably a permanent hot melt adhesive. One such adhesive is the hot melt adhesive HL-1358, manufactured by the H. B. Fuller Company of St. Paul Minn. The construction adhesive 56 may be applied in any pattern as is known in the art, including but not limited to lines, dots, spirals or a generally continuous layer of adhesive.

After the construction adhesive 56 is applied to the tape tab stock 70, the tape tab stock 70 is preferably directed to a second shear slitter 160 where the tape tab stock 70 is slit in a direction parallel to machine direction. The tape tab stock 70 is then separated at the slit by a tape tab stock spreader 162 and fed directly into a standard taper unit 170 as is commonly known in the art. One suitable taper unit, as supplied by Curt G. Joa, Inc of Sheboygan Falls, Wis., feeds the tape tab stock 70 to a vacuum anvil roll where the tape tab stock 70 is cut into individual tape tabs 40, spaced apart (slipped) and joined to the absorbent article.

Alternatively, the tape tab stock 70 may be rewound for storage or shipment and later fed into a taper unit on an absorbent article manufacturing line. If rewinding of the tape tab stock 70 is desired, it is preferred that the construction adhesive 56 have the ability to lose its adhesive properties during the period in which the tape tab stock 70 is wound and yet be able to reactivated upon demand at a later time. (As used herein, the term "reactivated" refers to the ability of an adhesive that has lost its adhesive properties to regain its adhesive properties at a later time.) Some nonlimiting examples of adhesives that have the ability to lose their adhesive properties and to be reactivated at a later time include hot melt adhesives, water activated adhesives, radiation activated adhesives and ultra-violet light activated adhesives.

Preferred Embodiments a. Two-piece tape tab

One preferred embodiment of the present invention for manufacturing a two-piece tape tab is depicted in FIGS. 3a–3f. As shown in FIG. 3a, a backing substrate 52, as described above, is provided having a longitudinal centerline L and a transverse centerline T perpendicular to the longitudinal centerline L. (As used herein, the term "longitudinal centerline" refers to an imaginary line that runs parallel to the machine direction. The "transverse centerline" runs perpendicular to the machine direction and parallel to the cross machine direction.) The backing substrate 52 further comprises a first surface 80, a second surface 82 opposed to the first surface 80, and a pair of outer longitudinal edges 84. (As shown in FIG. 3c, the backing substrate 52 further comprises a pair of inner longitudinal edges 83 once the backing substrate has been slit.)

FIG. 3b shows a plan view of the backing substrate 52 after it has passed the slot coater 130, having the pressure-sensitive adhesive 54 applied to the first surface 80. In a preferred embodiment, the pressure-sensitive adhesive 54 is not applied to the entire first surface 80 of the backing substrate 52. Rather, it is preferred that the pressuresensitive adhesive 54 be applied continuously to the backing substrate 52 in zones, preferably at least a first zone 86 and a second zone 88. (As used herein, the term "continuously" means a generally unbroken pattern.) The first zone 86 and the second zone 88 are preferably disposed transversely inwardly from the outer longitudinal edges 84 of the backing substrate 52. (As used herein, the term "transversely inwardly" means toward the longitudinal centerline L. The term "transversely outwardly" means away from the longitudinal centerline L.) The area between the outer longitudinal edges 84 of the backing substrate 52 and the zones 86 and 88 of pressure-sensitive adhesive 54 creates fixed regions 74 and 76. (These fixed regions 74 and 76 will be the portion of the tape tabs 40 that becomes permanently fixed to the chassis of the absorbent article.)

Figure 5:
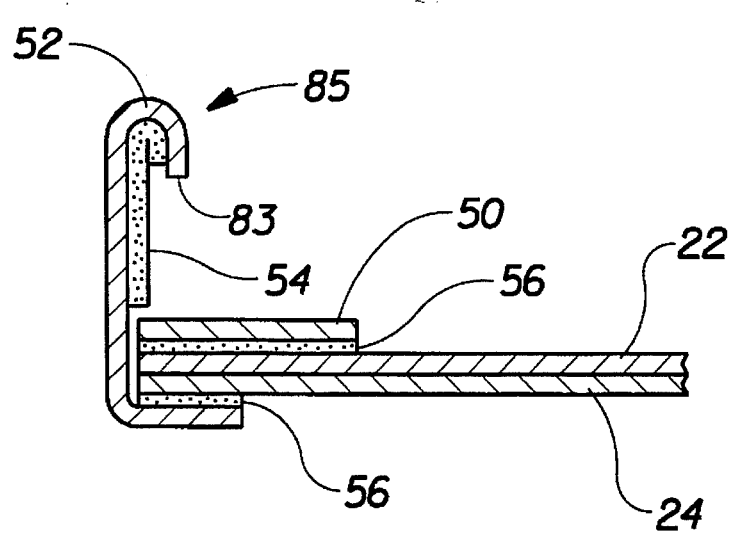
FIG. 5 is cross-sectional view of the two-piece tape tab produced by the method of the present invention.
Figure 6:
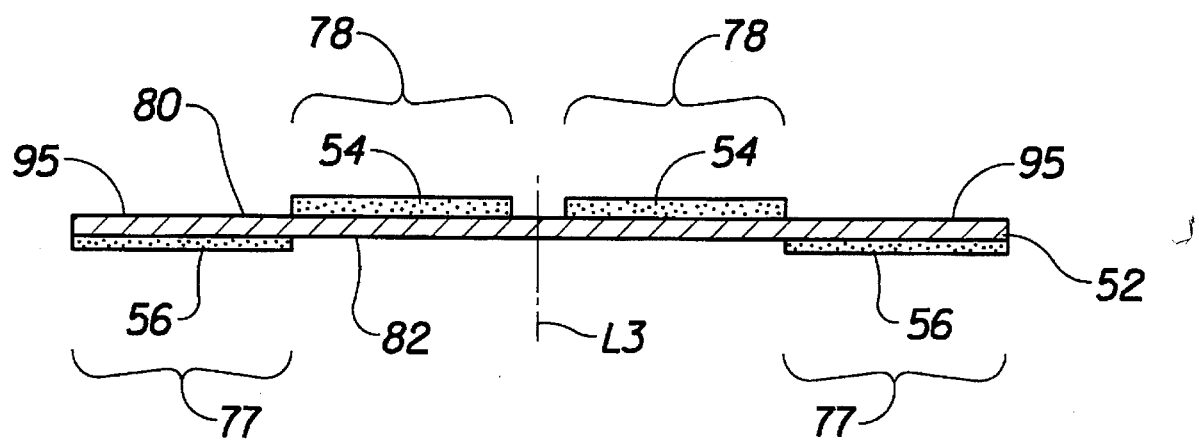
FIG. 6 is a cross-sectional view of the laminate that forms the one-piece tape tab embodiment produced by the method of the present invention.

The first zone 86 and the second zone 88 are also preferably transversely separated about the longitudinal centerline L. This leaves a non-adhesive area 75 between the first zone 86 and the second zone 88 that may be utilized as a release tab 85. The release tab 85, as shown in FIGS. 5 and 6 provides the user with a portion of the backing substrate 52 which is free of pressure-sensitive adhesive 54 and preferably not adhered to the release substrate 50 or any other element of the diaper 20. Thus, the user may grasp the release tab 85 and more easily open the tape tab 40. (As used herein, the term "open the tape tab" refers to separating the pressure sensitive adhesive 54 disposed on the tape tab 40 from the release substrate 50 or any other surface to which the pressure-sensitive adhesive 54 may be adhered.) However, if the first zone 86 and the second zone 88 are not transversely separated about the longitudinal centerline L, alternative methods of providing a release tab 85 are available. The methods include, but are not limited to folding a portion of the backing substrate 52 adjacent the inner longitudinal edges 83 onto the pressure-sensitive adhesive 54 disposed on the backing substrate 52 (shown in FIG. 5), or coating the backing substrate 52 adjacent the inner longitudinal edges 83 with a release agent or any other material that will prevent the pressure-sensitive adhesive 54 in the area adjacent the inner longitudinal edges 83 from adhering to the release substrate 50 or any other elements of the diaper 20.

As shown in FIG. 3c, the backing substrate 52 is preferably slit along the longitudinal centerline L, forming two backing substrate segments, 90 and 92. (Embodiments are contemplated, however, wherein more than two zones of pressure-sensitive adhesive 54 are applied to the backing substrate 52 and wherein the backing substrate 52 is slit and separated into more than two backing segments.) The backing substrate segments, 90 and 92, are preferably separated transversely before they are brought into contact with the release substrate 50 (shown in FIG. 3d).

The release substrate 50 has a release surface 94 and an adhesive surface 96 opposed the release surface 94. The release surface 94 is preferably comprises a release agent as described above, and is placed in contact with the pressure-sensitive adhesive 54 disposed on the first surface 80 of backing substrate segments 90 and 92. In a preferred embodiment, as shown in FIG. 3d, the release substrate 50 covers both the first zone 86 and the second zone 88 of pressure-sensitive adhesive 54; the first zone 86 being disposed on segment 90 and the second zone 88 being disposed on the segment 92 of the separated backing substrate 52. Further, in one preferred embodiment, as shown in FIG. 3d, at least a portion of the fixed regions 74 and 76 are not covered by the release substrate 50.

Once the release surface 94 of the release substrate 50 contacts the zones 90 and 92 of pressure-sensitive adhesive 54, the segments 90 and 92 of the backing substrate 52 become releasably joined to the release substrate 50, forming a laminate 60. The laminate 60, as shown in FIG. 3d, has an outer surface 62, an adhesive surface 64, a longitudinal centerline L1 and a transverse centerline T1. The adhesive surface 64 of the laminate 60 comprises the adhesive surface 96 of the release substrate 50 and the fixed regions 74 and 76 of the backing substrate 52 segments 90 and 92. As shown in FIG. 2, the laminate 60 is passed adjacent a spray nozzle 150 that applies a construction adhesive 56 to the adhesive surface of the laminate 60. The construction adhesive 56 may be applied to the entire adhesive surface 64 of the laminate 60. (FIG. 3e) In a preferred embodiment, however, the construction adhesive 56 is applied laterally inwardly from the longitudinal edges 84 up to about 0.02 inches (about 0.05 cm) to ensure the cleanliness of the process. (As noted above, the adhesive may be applied continuously or in any pattern.) The construction adhesive 56 preferably comprises a permanent, hot melt adhesive as described above.

After the construction adhesive 56 is applied to the adhesive surface 64 of the laminate 60, the laminate 60 is preferably slit along its longitudinal centerline L1 and separated to form tape tab stock 70, as shown in FIG. 3f. The tape tab stock 70 has a longitudinal centerline L2, a transverse centerline T2 perpendicular to the longitudinal centerline L2, an adhesive surface 102 and a non-adhesive surface 104. The tape tab stock 70 is preferably fed directly into the taper unit 170 that can be integrated into the absorbent article manufacturing line. The taper unit 170 cuts the tape tab stock 70 in a direction parallel to the transverse centerline T2 to form the individual tape tabs 40. The taper unit 170 then joins the adhesive surface 102 of the tape tabs 40 to individual absorbent articles manufactured concurrently with the tape tabs 40.

b. One-piece tape tab

Figure 7:
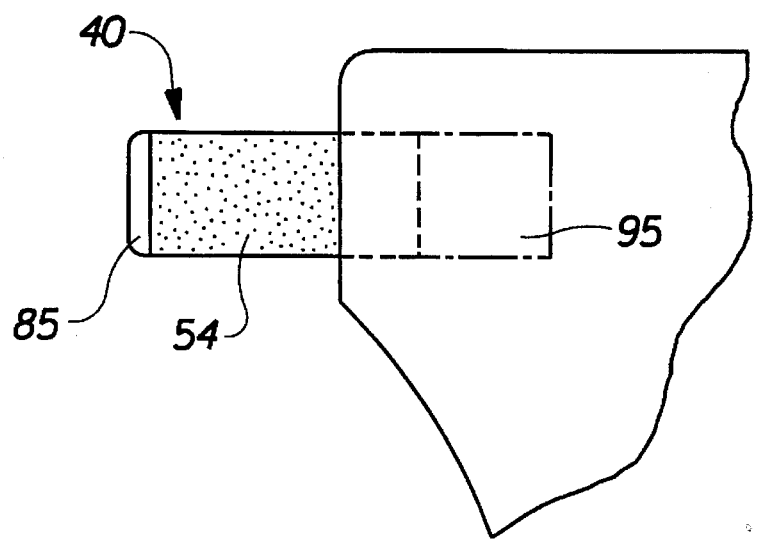
FIG. 7 is a plan view of a portion of an absorbent article comprising a one-piece tape tab embodiment produced by the method of the present invention.

In another preferred embodiment of the one-piece tape tab, as shown in FIG. 7, the tape tab 40 is joined to the chassis of the absorbent article with a permanent construction adhesive as described above with regard to the two-piece tape tab. In this embodiment, the steps described above relating to the preparation of a backing substrate 52 comprising zones 86 and 88 of pressure-sensitive adhesive 54 are followed. However, before the backing substrate 52 is slit and separated, a construction adhesive 56 is applied to the second surface 82 of the backing substrate 52. Preferably, the construction adhesive 56 is applied continuously to the backing substrate 52 in zones, rather than to the entire second surface 82 of the backing substrate 52. The zones of construction adhesive 56 are preferably transversely separated about the longitudinal centerline L3. Further, as shown in FIG. 6, the zones of construction adhesive 56 are preferably disposed transversely inwardly or transversely outwardly from the zones of pressure-sensitive adhesive 54. This ensures that at least a portion of the backing substrate 52 comprising the pressure-sensitive adhesive 54 can be folded over the first surface 80 of the backing substrate 52 to form a tape tab 40 once the backing substrate 52 is slit into segments.

The backing substrate 52 is preferably slit along the longitudinal centerline L3 and separated, forming at least two backing substrate segments as described above. These backing substrate segments are fed directly into a taper unit 170 which cuts the backing substrate segments into individual tape tabs 40. Each individual tape tab has a fixed end 77 and a releasable end 78. The releasable end 78 preferably comprises the pressure-sensitive adhesive 54 applied to the substrate backing 52. (In especially preferred embodiments, the releasable end comprises a release tab 85 as described above.) The fixed end 77 preferably comprises the construction adhesive 56 disposed on the second surface 82 and a release surface 95. The release surface 95 may comprise any release agent known in the art, including but not limited to, silicone, wax, or clay; or the release surface 95 may be formed by impregnating predetermined portions of the backing substrate 52 with a release agent, or by embossing or bonding the backing substrate 52 such that a release surface 95 is formed. Alternatively, a backing substrate 52 may be chosen that comprises areas of differing molecular structures, such as laminates or coextruded films, wherein at least a portion of the first surface 80 of the backing substrate 52 acts as a release surface 95.

Finally, the tape tab stock 70 is fed into a standard taper unit as is commonly known in the art. One such unit, as supplied by Curt G. Joa, Inc. of Sheboygan Falls, Wis., feeds the tape tab stock 70 to an anvil roll where the tape tab stock 70 is cut into individual tape tabs 40. The individual tape tabs 40 are then slipped (spaced) and the fixed end 77 of each tape tab 40 is joined to the chassis of the absorbent article by means of the construction adhesive 56 disposed on the second surface 82 of the backing substrate 52.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for manufacturing tape tab stock that may be used to form tape tabs for use with a disposable absorbent article, the method comprising the steps of:

providing a backing substrate having a first surface, a first longitudinal centerline, a transverse centerline perpendicular to said longitudinal centerline and a pair of longitudinal edges;

applying a pressure-sensitive adhesive to at least a portion of said first surface of said backing substrate;

slitting said backing substrate in a direction parallel to said longitudinal centerline to form at least two segments, each said segment having an inner longitudinal edge;

separating said segments in a direction parallel to said transverse centerline;

contacting a release substrate, having a release surface, an adhesive surface and a second longitudinal centerline, with said pressure-sensitive adhesive, such that said release surface covers said pressure-sensitive adhesive and forms a unitary laminate comprising said segments and said release substrate;

applying a construction adhesive to at least a portion of said adhesive surface of said release substrate;

slitting said laminate in a direction parallel to said longitudinal centerline; and separating said laminate into tape tab stock.

2. A method for manufacturing tape tab stock that may be used to form tape tabs for use with a disposable absorbent article, the method comprising the steps of:

providing a backing substrate having a first longitudinal centerline, a transverse centerline perpendicular to said longitudinal centerline, a first surface, and a pair of longitudinal edges;

applying a pressure-sensitive adhesive to said first surface of said backing substrate, said adhesive being applied in at least a first zone and a second zone, said first and second zones being transversely spaced apart and running continuously in a direction parallel to said longitudinal centerline of said backing substrate, said first and second zones being located on opposite sides of said longitudinal centerline and between said longitudinal centerline and said longitudinal edges wherein said first and second zones are spaced transversely inwardly toward said longitudinal centerline from said longitudinal edges such that an area formed adjacent to each of said longitudinal edges is free of said pressure-sensitive adhesive;

slitting said backing substrate between said first zone and said second zone, parallel to said longitudinal centerline to form at least two segments, each said segment having an inner longitudinal edge;

separating said segments in a direction parallel to said transverse centerline;

contacting a release substrate, having a release surface, an adhesive surface and a second longitudinal centerline, with said pressure-sensitive adhesive, such that said release surface covers said pressure-sensitive adhesive located in both said first zone and said second zone forming a unitary laminate comprising said segments and said release substrate;

applying a construction adhesive to at least a portion of said adhesive surface of said release substrate;

slitting said laminate between said segments in a direction parallel to said longitudinal centerline; and separating said laminate into a tape tab stock.

3. The method of claims 1 or 2 wherein said step of slitting said backing substrate comprises slitting said backing substrate coincident with said longitudinal centerline.

4. The method of claim 3 wherein said step of slitting said laminate comprises slitting said laminate coincident with said second longitudinal centerline.

5. The method of claims 1 or 2 further comprising the steps of:

cutting said tape tab stock into individual tape tabs, each having a permanently attached end and an refastenable end;

providing a chassis of an absorbent article; and securing said permanently attached end of said tape tab to said chassis with said construction adhesive.

6. The method of claim 1 or 2 further comprising the step of folding said inner longitudinal edges back over said first surface of said backing substrate to form release tabs, said folding step being performed before said release substrate is placed in contact with said backing substrate.

7. The method of claims 1 or 2 wherein said release substrate completely covers said backing substrate.

8. The method of claims 1 or 2 wherein the step of applying a construction adhesive to at least a portion of said adhesive surface of said release substrate includes applying said construction adhesive to at least a portion of said backing substrate.

9. The method of claim 8 wherein said construction adhesive applied to said backing substrate is applied laterally inwardly from said longitudinal edges up to about 0.05 cm.

10. The method of claim 8 further comprising the steps of:

cutting said tape tab stock into individual tape tabs, each having a permanently attached end and a refastenable end;

providing a chassis of an absorbent article; and securing said permanently attached end of said tape tab to said chassis with said construction adhesive.

11. The method of claim 10 wherein said construction adhesive applied to said backing substrate is applied laterally inwardly from said longitudinal edges up to about 0.05 cm.

12. A method for manufacturing tape tab stock that may be used to form tape tabs for use with a disposable absorbent article, the method comprising the steps of:

providing a backing substrate having a pair of longitudinal edges;

applying a pressure-sensitive adhesive to said first surface of said backing substrate;

contacting a release substrate, having a release surface and an adhesive surface, with said pressure-sensitive adhesive, such that said release surface covers said pressure-sensitive adhesive forming a unitary laminate; and applying a construction adhesive to at least a portion of said adhesive surface of said release substrate and at least a portion of said backing substrate forming a tape tab stock.

13. The method of claim 12 wherein said construction adhesive applied to said backing substrate is applied laterally inwardly from said longitudinal edges up to about 0.05 cm.

14. The method of claim 12 further comprising the steps of:

cutting said tape tab stock into individual tape tabs, each having a permanently attached end and a refastenable end;

providing a chassis of an absorbent article; and securing said permanently attached end of said tape tab to said chassis with said construction adhesive.

15. A method for manufacturing tape tab stock that may be used to form tape tabs for use with a disposable absorbent article, the method comprising the steps of:

providing a backing substrate having a pair of longitudinal edges;

applying a pressure-sensitive adhesive to said first surface of said backing substrate;

contacting a release substrate, having a release surface and an adhesive surface, with said pressure-sensitive adhesive, such that said release surface covers said pressure-sensitive adhesive forming a unitary laminate;

applying a construction adhesive to at least a portion of said adhesive surface of said release substrate and at least a portion of said backing substrate forming a tape tab stock, wherein said construction adhesive is applied laterally inwardly from said longitudinal edges up to about 0.05 cm;

cutting said tape tab stock into individual tape tabs, each having a permanently attached end and a refastenable end;

providing a chassis of an absorbent article; and securing said permanently attached end of said tape tab to said chassis with said construction adhesive.

* * * * *